United States Patent
Czajka, Jr. et al.

(10) Patent No.: US 10,667,879 B2
(45) Date of Patent: *Jun. 2, 2020

(54) MEDICAL DRAPE

(71) Applicant: Medline Industries, Inc., Mundelein, IL (US)

(72) Inventors: Francis A. Czajka, Jr., Libertyville, IL (US); Robert A. Lockwood, Libertyville, IL (US)

(73) Assignee: Medline Industries, Inc., Mundelein, IL (US)

(*) Notice: Subject to any disclaimer, the term of this patent is extended or adjusted under 35 U.S.C. 154(b) by 411 days.

This patent is subject to a terminal disclaimer.

(21) Appl. No.: 15/614,095

(22) Filed: Jun. 5, 2017

(65) Prior Publication Data
US 2017/0273751 A1    Sep. 28, 2017

Related U.S. Application Data

(63) Continuation of application No. 12/853,218, filed on Aug. 9, 2010, now Pat. No. 9,668,822.

(60) Provisional application No. 61/232,303, filed on Aug. 7, 2009.

(51) Int. Cl.
    *A61B 46/00*  (2016.01)
    *A61B 46/20*  (2016.01)

(52) U.S. Cl.
    CPC .............. *A61B 46/00* (2016.02); *A61B 46/40* (2016.02); *A61B 2046/201* (2016.02); *A61B 2046/205* (2016.02)

(58) Field of Classification Search
    CPC . A61B 19/10; A61B 2019/106; A61B 19/081; A61B 19/088; A61B 17/3431; A61B 17/0493; A61B 19/38; A61B 17/0293; A61B 19/087; A61B 46/40; A61B 46/30; A61B 2046/236; A61B 46/00; A61B 17/42; A61B 46/27; A61B 2046/205; A61B 50/36; A61B 2046/201; A61F 15/005;
    (Continued)

(56) References Cited

U.S. PATENT DOCUMENTS

| 3,310,459 A | 3/1967 | Guthrie et al. |
| 4,024,862 A | 5/1977 | Collins |
| 4,471,769 A | 9/1984 | Lockhart |

(Continued)

FOREIGN PATENT DOCUMENTS

| EP | 1237494 | 9/2002 |
| WO | WO 95/10986 | 4/1995 |

(Continued)

OTHER PUBLICATIONS

Examination Report dated Jan. 18, 2014 for Australian Application No. 2010279220.

(Continued)

*Primary Examiner* — Ophelia A Hawthorne
(74) *Attorney, Agent, or Firm* — Cooley LLP

(57) ABSTRACT

A medical drape is disclosed. The drape comprises a base drape portion and an insert drape portion removably attached to the base drape portion. A plurality of independently configured insert drape portions may be used, each insert being configured differently for a different procedure. The base drape portion may be made of environmentally friendly biodegradable material.

25 Claims, 9 Drawing Sheets

(58) Field of Classification Search
CPC ...... A61F 2013/530131; A61G 13/102; A41D 13/04
See application file for complete search history.

(56) References Cited

U.S. PATENT DOCUMENTS

| | | | |
|---|---|---|---|
| 5,010,899 | A | 4/1991 | Thompson |
| 5,163,931 | A | 11/1992 | Aldrett |
| 5,345,946 | A | 9/1994 | Butterworth et al. |
| 5,611,356 | A | 3/1997 | Rothrum |
| 5,614,298 | A | 3/1997 | Tanaka et al. |
| 5,783,504 | A | 7/1998 | Ehret et al. |
| 5,860,420 | A | 1/1999 | Wiedner et al. |
| 5,975,082 | A | 11/1999 | Dowdy |
| 6,083,602 | A | 7/2000 | Caldwell et al. |
| 6,105,578 | A | 8/2000 | Sommers et al. |
| 6,298,855 | B1 | 10/2001 | Baird |
| 7,384,588 | B2 | 6/2008 | Gordon et al. |
| 8,042,688 | B2 | 10/2011 | Parks et al. |
| 9,668,822 | B2 * | 6/2017 | Czajka, Jr. ............. A61B 46/00 |
| 2007/0048344 | A1 | 3/2007 | Yahiaoui et al. |
| 2009/0178685 | A1 | 7/2009 | Haines et al. |
| 2011/0030702 | A1 | 2/2011 | Czajka, Jr. et al. |

FOREIGN PATENT DOCUMENTS

| | | |
|---|---|---|
| WO | WO 99/04721 | 2/1999 |
| WO | WO 2007/109353 | 9/2007 |
| WO | WO 2011/017709 | 2/2011 |

OTHER PUBLICATIONS

Office Action dated Jun. 27, 2013 for Canadian Application No. 2,770,322.
Office Action dated Feb. 27, 2015 for Canadian Application No. 2,770,322.
Office Action for Canadian Application No. 2,770,322, dated Oct. 26, 2015.
Office Action for Canadian Application No. 2,770,322, dated Nov. 25, 2016, 3 pages.
Office Action dated Jan. 13, 2014 for Chinese Application No. 201080042155.1 (English translation).
Office Action dated Sep. 23, 2014 for Chinese Application No. 201080042155.1 (English translation).
Supplementary Partial European Search Report for European Application No. 10807296.8, dated Jul. 14, 2015, 7 pages.
Office Action for European Application No. 10807296.8, dated Jan. 27, 2017, 29 pages.
Mexican Office Action dated Nov. 28, 2014 for corresponding Mexican Application No. MX/a/2012/001609.
Mexican Office Action dated Jul. 10, 2015 for corresponding Mexican Application No. MX/a/2012/001609.
Office Action for Mexican Application No. MX/a/2012/001609, dated Mar. 7, 2016, 2 pages.
Office Action for U.S. Appl. No. 12/853,218, dated Nov. 19, 2015, 12 pages.
Office Action for U.S. Appl. No. 12/853,218, dated Jul. 10, 2014, 13 pages.
Office Action for U.S. Appl. No. 12/853,218, dated Jul. 12, 2012, 14 pages.
Office Action for U.S. Appl. No. 12/853,218, dated Jun. 16, 2016, 9 pages.
Office Action for U.S. Appl. No. 12/853,218, dated Feb. 6, 2015, 11 pages.
Office Action for U.S. Appl. No. 12/853,218, dated Aug. 1, 2013, 16 pages.
Office Action for U.S. Appl. No. 12/853,218, dated Dec. 7, 2011, 12 pages.
International Search Report and Written Opinion for International Application No. PCT/US2010/044915, dated Oct. 28, 2010.
International Preliminary Report on Patentability for International Application No. PCT/US2010/044915, dated Feb. 7, 2012.
Office Action for Canadian Application No. 2,770,322, dated Aug. 31, 2017, 3 pages.

* cited by examiner

MEDICAL DRAPE

This application is a continuation of U.S. patent application Ser. No. 12/853,218, now U.S. Pat. No. 9,668,822, entitled "Medical Drape," filed on Aug. 9, 2010, which claims priority to the commonly owned U.S. Provisional Patent Application No. 61/232,303, entitled "Medical Drape," filed on Aug. 7, 2009, which are incorporated herein by reference in their entireties.

FIELD OF THE INVENTION

Embodiments of this invention relate to medical drapes, and more specifically to environmentally friendly medical drapes used in connection with medical procedures. Embodiments of the invention also relate to medical drapes having a alternative insert attached insert portions making the drape adaptable to multiple procedures while reducing hazardous waste and improving inventory management.

BACKGROUND OF THE INVENTION

Medical drapes are widely used during the performance of surgical and other medical procedures. The drapes are used to cover a patient as a patient protective measure. The drapes may be sterilized and are intended to prevent the possibility of patient infection. The drapes provide protection to the patient by creating a sterile environment surrounding the surgical site and maintaining an effective barrier that minimizes the passage of microorganisms between non-sterile and sterile areas. Drapes have generally been made of a material that is resistant to blood, plasma, serums, and/or other bodily fluids to prohibit such fluids from contaminating the sterile field.

Drapes are generally configured to specifically accommodate the particular surgical procedure to be performed, resulting in a need for surgical facilities to stock multiple drapes of different sizes and shapes. Some drapes have a common over all shape but have specific surgical portions designed for the particular surgery. Accordingly, surgical facilities must maintain inventories of multiple drapes that are the same size and shape but having specific surgical portions. Because the drapes may be very large, each drape uses considerable space during storage and increases the complexity of inventory management.

The drape must be large enough to sufficiently cover the patient in accordance with the surgical procedure. Many drapes are large enough to cover the entire patient and may cover other equipment adjacent to the patient. The drape's overall size may be large while the actual portion where a procedure is performed is small, or at least small relative to the overall drape size because the drape must be large enough to protect against infection. As a result, much of the drape may not become soiled during the surgical procedure or as it is removed from the procedure area.

In many instances, once the procedure is complete, the entire drape must be deposited in a bio-hazard disposal container in accordance with biological hazardous waste guidelines even though only a small portion of the drape is sufficiently soiled to require bio-hazard disposal. Consequently, large amounts of unsoiled non-hazardous material are disposed of in a hazardous waste process. Bio-hazardous waste is more costly and difficult to handle because of increased risk of infection and biological hazardous waste guidelines. Surgical facilities incur the cost of disposing of large amounts of material in accordance with biological hazardous waste guidelines even though the material is unsoiled and non-hazardous.

Moreover, even when a drape is not sufficiently soiled to require hazardous disposal, existing drapes are currently made of non-biodegradable material. As a result, the entire drape becomes waste that must be disposed of in a non evironmentally friendly manner.

Thus, it would be desirable to have a medical drape that is environmentally friendly, reduces waste and improves inventory management.

BRIEF DESCRIPTION OF DRAWINGS

The foregoing and other advantages of the invention will become apparent upon reference to the following drawings and detailed description.

Figure 1:
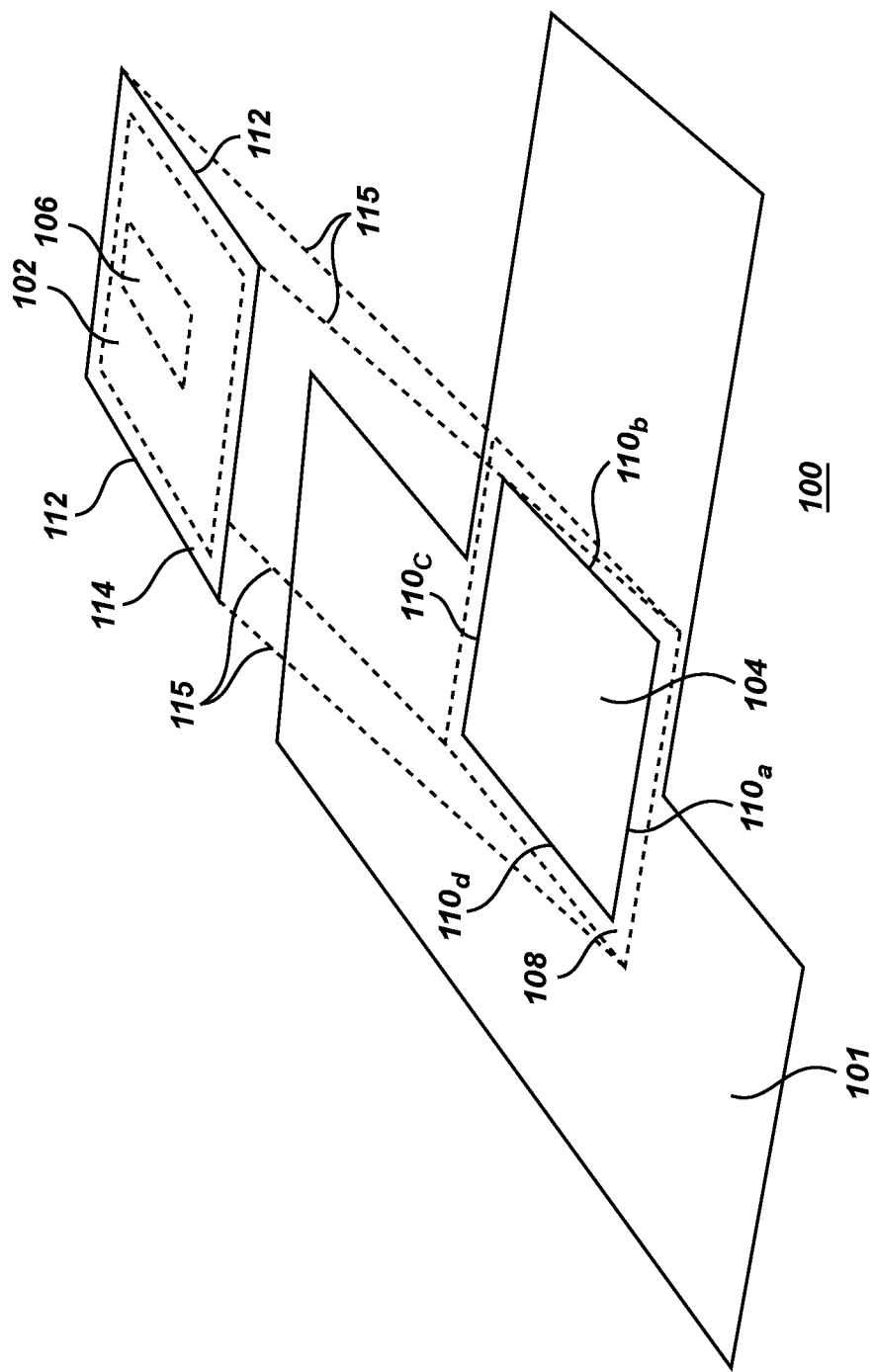
FIG. 1 is an exploded perspective view of a medical drape according to one embodiment of the invention.

While the invention is susceptible to various modifications and alternative forms, specific embodiments are shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION

As embodiments of the invention are now described in detail, referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Unless otherwise indicated, the terms "attach," "connect," "couple" and "secure" may refer to either a permanent or a separable attachment between two elements directly connected or connected by way of an intermediate element.

Embodiments of the invention provide a modular drape system that improves waste handling, reduces inventory space and overall provides for an environmentally friendly infection control device. In one embodiment, the system incorporates a base drape portion and an insert drape portion. The insert portion may be specifically adapted to a particular surgical procedure. The insert drape portion is attached to the base drape portion to form a unitary drape. Subsequent to surgery, the insert drape portion is removed from the base drape portion and disposed of in a first waste container while the base drape portion is disposed of in a second waste container. The insert drape portion can be removed post procedure and disposed of in traditional medical/bio-hazardous waste, leaving the larger base drape portion to be disposed of as standard waste.

Embodiments of the present invention provide that the base drape portion comprises a biodegradable material. In other embodiments, both the base portion and the insert portion may be biodegradable. Alternatively one or both portions may comprise woven or non woven material. In other embodiment, the base drape portion is re-useable while the insert portion is disposable. In yet another embodiment the base drape portion is disposable while the insert drape portion is re-useable.

Embodiments of the invention also provide for a single material drape wherein substantially all of the drape material is biodegradable. The drape portions in these embodiments need not be separable and the entire drape may form a single unit. Alternatively, the entire drape may form a single unit, but an insert drape portion may be removable. For example, the insert drape portion may be surrounded by perforations such that the insert portion is removable after use by tearing the drape at the perforations.

Embodiments of the present invention offer an advantage over prior art systems because the modular structure provides a complete system that when combined, forms a single drape that can be separated after use. As noted above, the prior art systems use one piece drapes, wherein the entire drape is disposed of as costly bio-hazardous waste. In embodiments of the invention, only a smaller insert drape portion is disposed of as bio-hazardous waste. In addition, inventory management is improved because a common base drape portion may be used together with a variety of insert drape portions so that fewer stock-keeping units need to be maintained and more shelf space is available.

Another advantage of the present invention over the prior art is that the drape may have at least a portion that is biodegradable. This significantly reduces the amount of non-biodegradable waste that must be handled and which enters landfills. In some embodiments the drape may be made of substantially all biodegradable materials. The drape materials may be made from wood pulp or other biodegradable products instead of the typical polypropylene or spunlace of the prior art. Alternatively, the drape material may be made of typical polypropylene or spunlace of the prior art however treated with an additive that renders the material biodegradable. Drapes could also be made with non biodegradable components securely fastened to the base drape portion with the understanding that 75-85% of the product may be biodegradable.

Medical drapes as illustrated and described herein are generally shown as they would appear after being unfolded and ready for use in a surgical or medical procedure (for example, catheterization, angiography or radiology). The front of the drape is generally referred to as the side of the drape that is facing the medical person and the back of the drape is the side that is adjacent to the patient's skin. It may be desirable that the drape have dimensions suitable for covering the patient's entire body, including, in some embodiments, the patient's head and face to assist in maintaining the sterility of the surgical area and thereby lower the risk of infection. In such embodiments, the total length of the drape may be as long as about 125 in. In other embodiments, the drape may cover less than the patient's entire body and may have a length generally from about 30 in. to about 50 in. The total width of the drape is generally up to about 80 in. These dimensions are by way of example only and do not limit the disclosure as drapes come in various sizes and shapes.

The term surgery and procedure may be used interchangeably throughout this disclosure however it is understood that some procedures may not be surgical, per se. The drape system of the instant disclosure is not intended to be limited to surgical situations but situations wherein a drape may be used on a patient as a protection barrier for a variety of reasons, including for infection control. The term drape is know to those of ordinary skill in the art but may also be referred to as a barrier, sterile field, procedural drape and the like and for the purposes of the present invention these and other like terms may be interchangeable as would be apparent to one of ordinary skill in the art.

Figure 2:
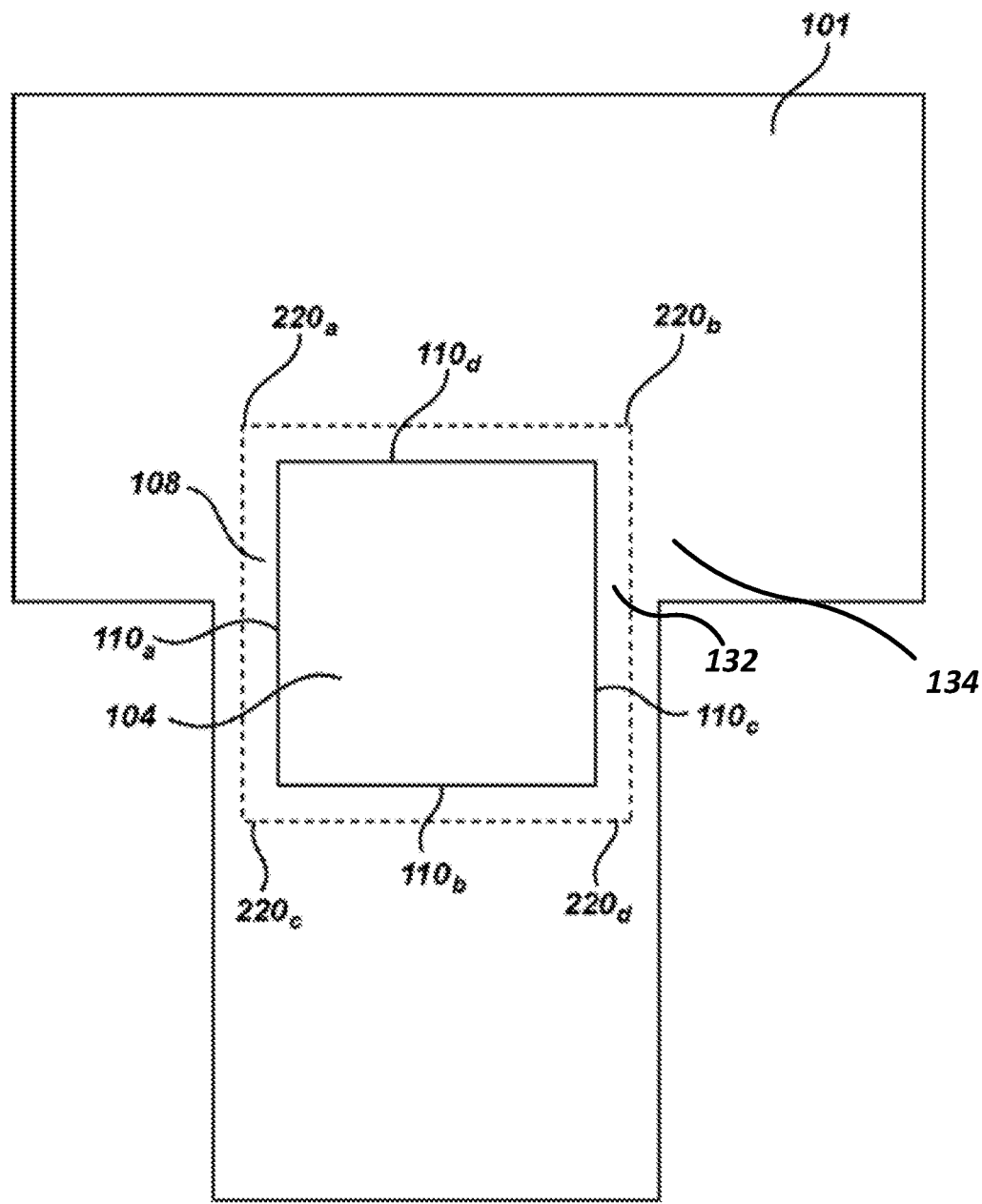
FIG. 2 is a plan view of a front side of a base drape portion according to the embodiment shown in FIG. 1.
Figure 3:
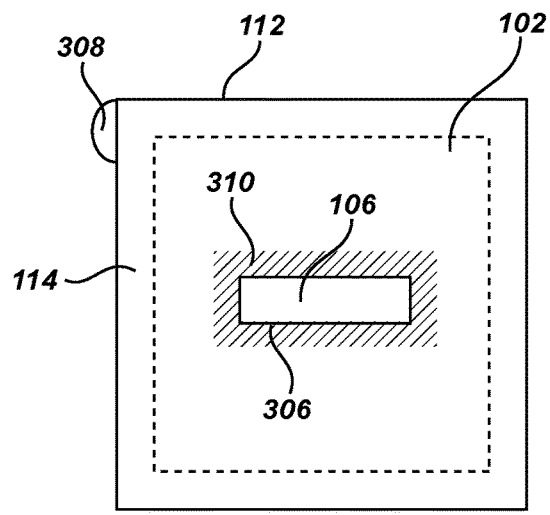
FIG. 3 is a plan view of a front side of an insert drape portion according to the embodiment shown in FIG. 1.

An embodiment of the drape system is illustrated in FIGS. 1-3. FIG. 1 shows an exploded view of the drape 100, including a base drape portion 101 and an insert drape portion 102. The base drape portion 101 having a void 104 formed therein for removably attaching the insert drape portion 102 as indicated by the dotted lines 115. The void 104 may be of a standardized size to accept various different types of insert portion 102, each type specifically adapted to a different procedure. FIG. 2 illustrates a plan view of the base drape portion 101. FIG. 3 illustrates a plan view of an insert drape portion 102 that is design specifically for a particular medical or surgical procedure.

The base drape portion 101 and the insert drape portion 102 may be assembled prior to the procedure and may be assembled prior to delivery to the operating room or location where the procedure is performed. In another embodiment the base drape portion 101 and the insert drape portion 102 may be assembled as part of the procedure or during the preparations for the procedure through the use of a selective securement element. Generally, when the drape is a part of the sterile field, the drape is assembled as part of the procedure preparation.

The base drape portion 101 may be a universal drape portion or drape blank that is configured such that it that may not be procedure specific, or may at least be used for a variety of procedure types. For example, many procedures require the entire patient to be covered by a drape; in this embodiment, these procedures may all use a base drape portion having a standard base drape portion shape. Depending on the surgical procedure to be performed, a procedure-specific insert drape portion is selected to be removably attached to the base drape portion 101. In general, the base drape portion 101 is not used alone and is combined with another drape portion or apparatus in order to perform the procedure.

The base drape portion 101 may be made of a first material, and the insert drape portion 102 made of a second material. For example, in one embodiment, the base drape portion 101 may be made with a biodegradable material and the insert drape portion 102 made with a non-biodegradable material. To provide adequate protection, the insert drape portion 102 material may be any material usable in a healthcare environment that is effective in providing a barrier to the surgical or procedural site for personal protection. To be effective, the material is generally made of a water-repellent or water-impermeable material and/or is coated with a water-repellent or water impermeable material to prevent the passage of bodily fluids and/or contaminating microorganisms. For example, the insert portion 102 may be made of various woven, non-woven, and/or hydroentangled materials. The base fabrics used may include Airlaid, meltblown, spunlace and blends of polyester, polypropylene, and polyethylene, or any combination thereof.

In one embodiment, the drape 100 may be a single piece formed of biodegradable material, the biodegradable material has a high cellulose content, and meets ANSI/AAMI PB70, Level 2 barrier requirements. For example, the drape material may be a cellulose material such as a wood pulp. In one embodiment the first drape comprises a cellulose content greater than 60%. In another embodiment, the drape material comprises greater than 80% cellulose. In general the biodegradable material is environment friendly and decomposes such that the drape is compostable, yet fulfills at least level 2 barrier protection requirements.

An example of an appropriate drape material that may be used in embodiments of the invention is provided by Arjowiggins Healthcare, 20, rue Rouget de Lisle, 92442 Issy-les-Moulineaux, France. Test results using this material include the following:

Water Resistance: Impact Penetration Test—performed in accordance with MTCC Test Method 42-2007. Water Resistance: Impact Penetration Test, American Association of Textile Chemists and Colorists, Research Triangle Park, N.C.; WSP 80.3 (05), Standard Test Method for the Evaluation of Water Penetration (Spray Impact Test) of Nonwoven Fabrics, International Nonwoven & Disposables Association, Cary, N.C.; ANSI/AAMI PB70:2003, Liquid barrier performance and classification of protective apparel and drapes intended for use in health care facilities, Association for the Advancement of Medical Instrumentation, Arlington, Va.

TABLE 1

Water Resistance: Impact Penetration Test

| SAMPLE NUMBER | VISUAL PENETRATION | AMOUNT OF PENETRATION (g) |
|---|---|---|
| 1 | Yes | 0.18 |
| 2 | Yes | 0.14 |
| 3 | Yes | 0.15 |
| 4 | Yes | 0.06 |
| 5 | Yes | 0.19 |
| 6 | Yes | 0.15 |
| 7 | Yes | 0.10 |
| 8 | Yes | 0.11 |
| 9 | Yes | 0.14 |
| 10 | Yes | 0.10 |
| 11 | Yes | 0.10 |
| 12 | Yes | 0.19 |
| 13 | Yes | 0.11 |
| 14 | Yes | 0.12 |
| 15 | Yes | 0.19 |
| 16 | Yes | 0.17 |
| 17 | Yes | 0.13 |
| 18 | Yes | 0.13 |
| 19 | Yes | 0.13 |
| 20 | Yes | 0.10 |
| 21 | Yes | 0.11 |
| 22 | Yes | 0.10 |
| 23 | Yes | 0.13 |
| 24 | Yes | 0.09 |
| 25 | Yes | 0.10 |
| 26 | Yes | 0.09 |
| 27 | Yes | 0.13 |
| 28 | Yes | 0.11 |
| 29 | Yes | 0.09 |
| 30 | Yes | 0.08 |
| 31 | Yes | 0.09 |
| 32 | Yes | 0.10 |
| Average | N/A | 0.12 |
| Negative Control | None Seen | 0.01 |

Water Resistance: Hydrostatic Pressure Test—performed in accordance with AATCC Test Method 127-2008, Water Resistance: Hydrostatic Pressure Test, American Association of Textile Chemists and Colorists, Research Park Triangle, NC; INDA 1ST 80.6 [WSP 80.6 (05)].2005, Standard Test Method for the Evaluation of Water Resistance (Hydrostatic Pressure) Test, International Nonwoven & Disposables Association, Cary, N.C.; ISO 811-1981, Resistance of Fabrics to Penetration by Water (Hydrostatic Head Test), International Organization for Standardization, Geneva, Switzerland; ISO 139. 2ED 2005, Textiles-Standard Atmospheres for Conditioning and Testing, International Organization for Standardization, Geneva, Switzerland; ANSI/AAMI PB70:2003, liquid barrier performance and classification of protective apparel and drapes intended for use in health care facilities, Association for the Advancement of Medical Instrumentation, Arlington, Va.

TABLE 2

Water Resistance: Hydrostatic Pressure Test

| SAMPLE NUMBER | FAILURE PRESSURE (cm H$_2$O) |
|---|---|
| 1 | 54.5 |
| 2 | 55.0 |
| 3 | 55.0 |
| 4 | 54.5 |
| 5 | 54.0 |
| 6 | 53.5 |
| 7 | 54.0 |
| 8 | 52.5 |

TABLE 2-continued

Water Resistance: Hydrostatic Pressure Test

| SAMPLE NUMBER | FAILURE PRESSURE (cm H$_2$O) |
|---|---|
| 9 | 52.0 |
| 10 | 52.5 |
| 11 | 54.5 |
| 12 | 53.0 |
| 13 | 52.0 |
| 14 | 55.0 |
| 15 | 56.0 |
| 16 | 55.0 |
| 17 | 52.5 |
| 18 | 53.5 |
| 19 | 54.0 |
| 20 | 53.5 |
| 21 | 56.0 |
| 22 | 55.0 |
| 23 | 56.0 |
| 24 | 52.0 |
| 25 | 51.0 |
| 26 | 50.5 |
| 27 | 52.0 |
| 28 | 53.0 |
| 29 | 49.5 |
| 30 | 56.0 |
| 31 | 53.0 |
| 32 | 54.5 |
| Average | 53.6 |

Biodegradation Test—performed in accordance with ASTM D 5511-02 at a temperature of 52±2° C. According to the ASTM D 5511-02 guideline, the test is considered valid if a) the degree of biodegradation of the material is >70% after 15 days, and b) the deviation of the percentage of biodegradation for the reference item in the different vessels is less than 20% at the end of the test. The exemplary Arjowiggins material fulfills both criteria. The final biodegradation result obtained after 15 days was 86.3±0.7% or 96.6% relative to the reference Cellulose.

TABLE 3

Average Biodegradation Percentages after 15 Days

| Test item | Average $C_{input}$ | Average $C_{gaseous}$ | Biodegradation (%) AVG | STD | 95% CL |
|---|---|---|---|---|---|
| Cellulose | 6.6 | 5.9 | 89.3 | 5.4 | 10.3 |
| Drape material | 6.4 | 5.6 | 86.3 | 0.7 | 2.2 |

Figure 17:
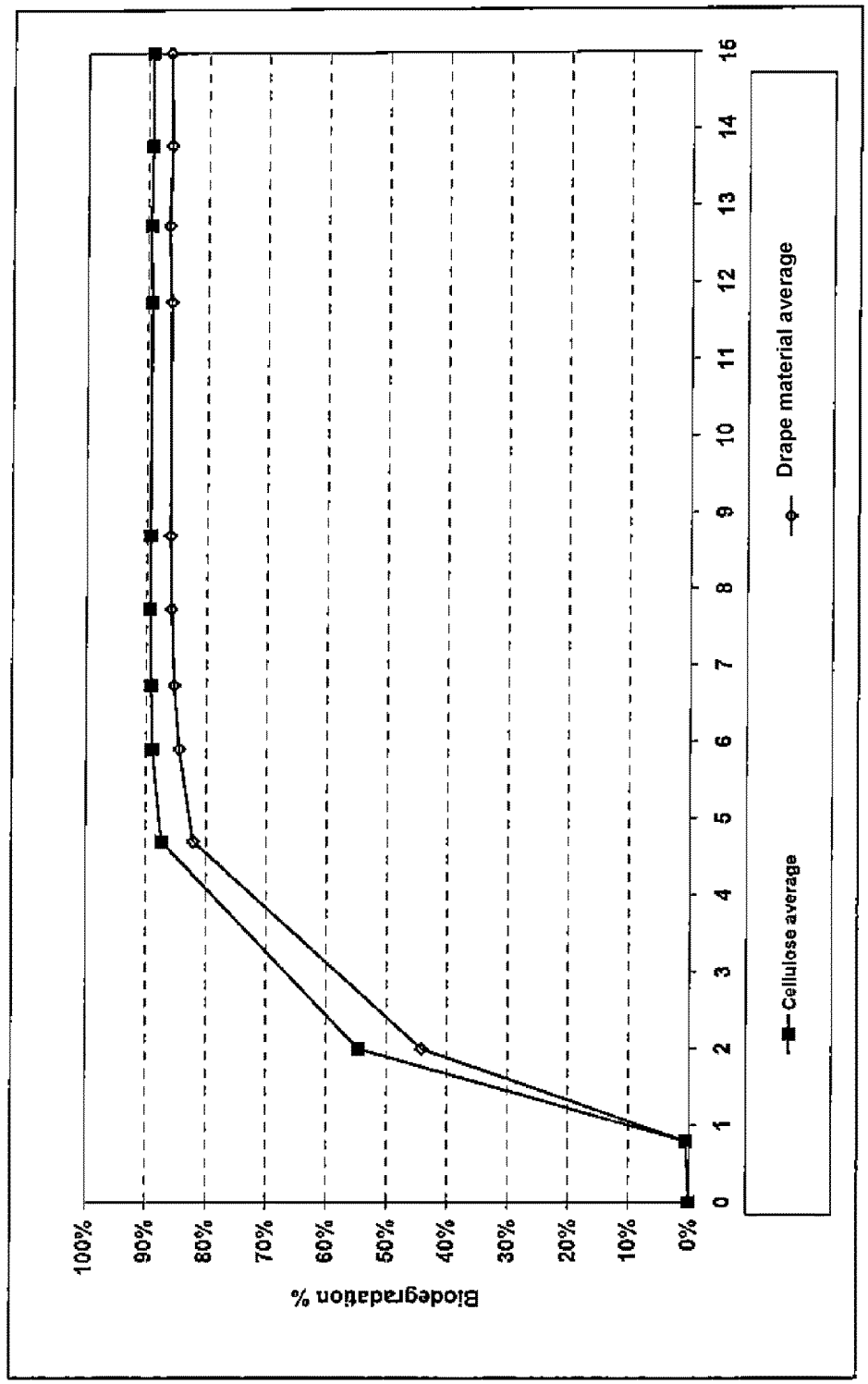
FIG. 17 is a chart showing the average biodegradation of the exemplary biodegradable drape material according to an embodiment of the invention as compared to a reference Cellulose material.

FIG. 17 shows the average biodegradation of the exemplary biodegradable drape material as compared to the reference Cellulose over the time period of the test.

An embodiment of the biodegradable drape material may have the properties shown in Table 4.

TABLE 4

Properties of an Exemplary Biodegradable Drape Material

| PROPERTIES | UNITS | STANDARDS OR METHODS | TYPIC | min | Max |
|---|---|---|---|---|---|
| Substance | g/m2 | ISO 536 | 75 | 70 | 80 |
| Hydrohead | cm | ISO 811 | 55 | 35 | 75 |
| Burst strength | Psi | ISO 2758 | 25 | 14 | 36 |
| Wet Burst | Psi | ISO 3689 | 11 | 8 | 14 |
| Dry tensile MD | kN/m | ISO 1924-2 | 2.20 | 1.60 | 2.80 |
| Dry tensile CD | kN/m | ISO 1924-2 | 2.00 | 1.30 | 2.70 |
| Stretch MD | % | ISO 1924-2 | 14 | 7 | 20 |
| Stretch CD | % | ISO 1924-2 | 4 | 3 | 6 |
| Wet tensile MD | kN/m | ISO 3781 | 0.67 | 0.30 | 1.05 |
| Wet tensile CD | kN/m | ISO 3781 | 0.60 | 0.23 | 1.00 |
| Tear strength MD | mN | ISO 1974 | 1250 | 900 | 1600 |
| Tear strength CD | mN | ISO 1974 | 1350 | 1000 | 1700 |
| Drape MD | — | EN 868-2 (app. D) | 70 | | 90 |
| Drape CD | — | EN 868-2 (app. D) | 180 | | 200 |

The drape material may be unbleached, removing typical bleaching products, such as sodium hypochlorite for example, from the process of manufacturing the drape material and further enhancing the drape's environmentally friendly characteristics. The flouro-chemicals typically used in drapes, which create or enhance the repellency of the drape, may also be removed, eliminating fluorocarbons from the manufacturing process. The drape material may be a fluorocarbon free and bleach free processed material which reduces negative impact on the environment. Further, the drape material may be free of chemical binders, additives or dyes. In addition the drape material may be disposed of in landfills as the material decomposes as opposed to plastics including spunbound and meltblown products (commonly known as SMS, spunbound-meltblown-spunbound) which do not readily decompose, if at all.

In another embodiment, the drape 100 may be a single drape portion that is separable into a base portion and a removable portion. Both drape portions are made from the same material, either biodegradable (as discusses above) or non biodegradable. However, the drape portions are separable. For example, a single material drape is formed into portions by defining a second drape portion at a predetermined or preformed separation area of the drape to form a removable portion in the drape at a predetermined procedure area. Subsequent to the procedure, the removable portion of the drape is separated from the first drape portion at the defined separation area. The separation area includes a mechanism to separate the two portions such as perforated drape material or some other appropriate mechanism. In this embodiment, the base portion of the drape does not come in contact with the fluids resulting from the procedure and can be disposed of accordingly, while the removable portion, which has come in contact with the fluids resulting from the procedure, may be disposed of as bio-hazardous waste. In this embodiment the entire drape may be made of biodegradable material.

In one embodiment, the drape may comprise first and second drape portions that are discrete units or modules such as a base drape portion and an insert drape portion. In this embodiment, the insert drape portion 102 is removably attached to the base drape portion 101, which is a drape blank, having a void 104. The insert drape portion 102 may have a perimeter that has the same or different shape then that of the void 104.

As shown in FIGS. 1-4, the base drape portion 101 comprises a first securement area 108. The void 104 of the base drape portion 101 is adjacent to the first securement area 108. The insert drape portion 102 has a size and shape that is configured to be coincident with the size and shape of the void 104 of the base drape portion 101. The insert drape portion 102 includes a second drape securement area 114 for removably attaching to the first securement area 108 of the base drape 101, effectively coupling the drape portions together to form the drape 100.

The insert drape portion 102 may further comprise a procedural site 106, also known as the critical zone, at which the procedure takes place. In this embodiment the procedure site 106 is a fenestration, which in general is an opening having a predetermined shape and size particular to performing a specific procedure.

The void 104 of the base drape portion 101 may be configured in size and shape to receive one of a plurality of independently configured insert drape portions 102, each of the plurality of insert drape portions 102 being configured differently for different procedures. For example, the base drape portion 101 may have a standard outer drape shape, formed by a first drape perimeter, having arm boards in one embodiment, and may be used for multiple surgery types. Assembled together, the base drape portion 101 and the insert drape portion 102 form the complete drape 100. Said another way, one base drape portion 101 accommodates and receivably attaches to one of a plurality of surgery specific insert drape portions 102 to form a complete drape 100 for at least one specific procedure. The insert drape portion 102 is selected based on the medical or surgical procedure and is attached to the base drape portion 101 in order to perform the procedure. For example, a base drape portion 101 may receive a laparotomy insert drape portion 702; a cholecystectomy insert drape portion; a cardiovascular incise insert drape portion 802; a cyctoscopy insert drape portion 1002; a c-section insert drape portion 1102; and the like. These specific insert drape portion types are by way of example only and those of ordinary skill in the art will appreciate that a plurality of surgery or medical procedure specific drapes may be incorporated into the insert drape portion and secured to a base drape portion.

The base drape portion 101 and the insert drape portion 102 overlap, such that the insert drape portion edge 112, extends beyond the void 104 over at least one edge 110a, 110b, 110c, 110d of the void 104. At least one edge 112 of the insert drape portion 102 overlaps with an edge 110 of the void 104, forming the coincident securement areas 108, 114 of the respective drape portions. The void 104 in one embodiment is a rectangular opening within the base drape portion 101 with an "x" dimension of approximately fifteen inches and a "y" dimension of approximately fifteen inches. The exact size of the void 104 may be adjusted based on design consideration, however the void size remains coincident with the complimentary insert drape portion size and shape. For example the insert drape portion 102 in this embodiment is also square in shape and has "x" and "y" dimensions greater than fifteen inches so that the two overlap and may be secured together at the overlap. For example, the size of the second drape portion in this embodiment may be seventeen in each of the "x" and "y" dimensions. In another embodiment, the "x" dimension is greater than the "y" dimension or vice versa. In other words, the "x" dimension of the insert drape portion 102 is greater than the "x" dimension of the void 104, and the "y" dimension of the insert drape portion 102 is greater than the "y" dimension of the void 104. In this embodiment, the edge 112 of the insert drape portion 102 extends beyond the perimeter 110 of the void 104 at all points about the void.

Figure 4:
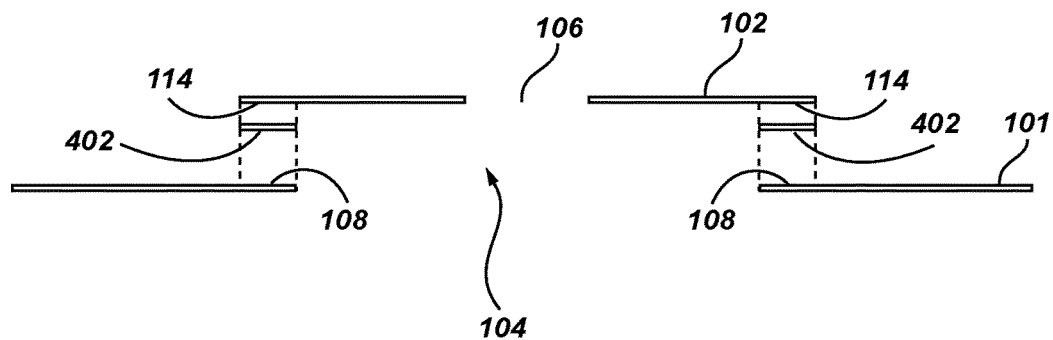
FIG. 4 is a cross sectional exploded view of a drape according to an embodiment of the invention.

As shown in FIG. 4, the securement area 108, 114 may be coincident with the overlap between the base drape portion 101 and the insert drape portion 102. The securement area 108 of the base drape 101 or the securement area 114 of the insert drape 102 may have a securement element 402 that allows the insert drape portion 102 to be removably coupled to the base drape portion 101. For example, in one embodiment, the securement element 402 is an adhesive applied to one of the securement areas. A release liner (not shown) is applied over the adhesive to protect the adhesive from getting dirty and from unwanted adhesion prior to assembly of the two drape portions. In the embodiment shown in FIG. 4, the securement element 402 is initially carried on the securement area 114 of the insert drape portion 102. The adhesive may be a pressure sensitive adhesive (PSA) or any other adhesive that may secure the two drape portions together in a removable fashion. For example, an refastenable adhesive such as used in adhesive note type applications may be used or any similar adhesive that allows the drapes to be separated subsequent to the procedure.

In another embodiment a non-refastenable adhesive may be used in combination with a perforated base drape portion. In this embodiment the base drape portion 101 is perforated adjacent to the securement area 108. The insert drape portion is secured to the base drape portion 101 with the adhesive. Post procedure, the two drape portions (e.g., a first base drape portion 132 (also referred to as an inner portion) and a second base drape portion 134 (also referred to as an outer portion)) are separated at the perforations. The adhesives may be acrylic based, hot melt or any appropriate medical grade adhesive known to those of ordinary skill in the art.

In yet another embodiment, both the base drape portion 101 and the insert drape portion 102 have a first securement element and a second securement element respectively. For example, both the first securement element and the second securement element may be an adhesive or a set of hook and loop fastening components or the like.

In yet another embodiment, the securement element is applied to the securement area 114 of the insert drape portion 102 and extends beyond the securement area. The size and shape of the application of the securement element is configured such that the securement element will come in contact with both the base drape portion, coupling the base drape portion to the insert drape portion, and the patient, coupling the insert drape portion 104 to the patient.

Figure 5:
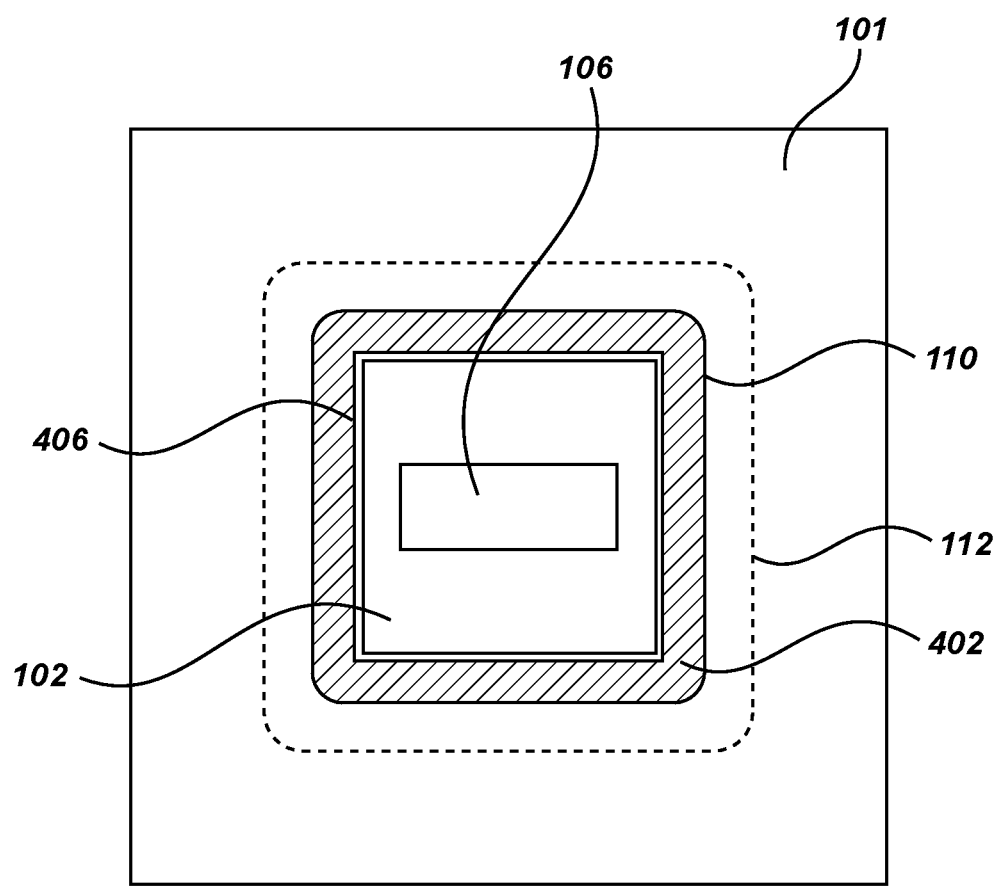
FIG. 5 is a plan view of a back side of a medical drape according another embodiment.

In still another embodiment, FIG. 5 illustrates the back side of a drape 100 having the base drape portion 101 attached to the insert drape portion 102. The outer perimeter 112 of the insert drape portion 102 is shown in dotted line as it is on the other side of the drape facing away in this illustration. In this embodiment, the securement element 402 (cross-hatch) on the insert drape portion is configured to only come in contact with the patient when the second drape portion is coupled to the first drape portion. In this embodiment, the securement element 402 may comprise a sealing element 406, providing a seal to prevent fluids from the procedure site (critical zone) from flowing beyond the sealing element. In this embodiment the sealing element 406 prevents the fluid from coming into contact with the base drape portion 101. Without the bodily fluids on the base drape portion, the base drape portion does not become contaminated and therefore does not need to be treated as bio-hazardous material. Consequently, the base drape 101 may be disposed of in traditional garbage sources and not in costly bio-hazard waste containers.

Returning to FIG. 2, the base drape portion is shown from a front view. Here the alignment or registration between the base drape portion 101 and the insert drape portion 102 is shown. Base drape indicia 220a, 220b, 220c, 220d on the base drape portion 101 help during manual alignment when securing the insert drape portion 102 to the base drape portion 101. All four registration indicia are not necessary and the shape and form of the indicia may depending upon the configuration of the drape portions. For example, the registration indicia may be two dots in adjacent corners. Alignment instructions may be printed on the drape with surgical grade ink or the like or have orientation markers, i.e. align a "1" on the base drape portion and a "1" on the insert drape portion, to ensure that the insert drape portion is applied to the base drape portion in the proper orientation.

As shown in FIG. 3, the procedural site 106 of the insert drape portion 102 in one embodiment has an adhesive 310 on the body side of the drape to secure the procedural site to the patient. The procedural site in one embodiment is defined by a perimeter 306. The adhesive is adjacent to a procedural site perimeter 306, which may be an edge of the fenestration, extending toward the outer edge of the insert drape portion 102. In one embodiment, the procedural site adhesive extends away from the procedural site to at least one edge of the insert drape portion such that the procedural site adhesive couples the insert drape portion to the base drape portion.

In one embodiment, the base drape portion 101 is donned on the patient, such that the void 104 is positioned to expose the surgical site to the medical personnel. The insert drape portion 102 is removably secured to the base drape portion 101 by removing a protective liner covering the securement element 402, and removably securing the insert drape portion 102 to the first drape 101, effectively covering the void 104 with the insert drape protion 102. A medical procedure is performed at or though the surgical site 106, a fenestration in this embodiment, of the insert drape portion 102. The drape 100 may also be maintained for non-fenestrated drapes, split drapes, universal drape sets, drapes with arm board covers, drapes without arm board covers and the like. It is to be understood that the drape system is not limited to any particular procedure or type or category of drape.

The insert drape portion 102 may have at least one separation assistance member 308. The separation assistance member may be a tab extending from the insert drape portion 102 that the user can grab in order to pull and apply force to the insert drape portion 102 to separate it from the base drape portion 101. In another embodiment the separation assistance member comprises a reinforced edge formed into at least one edge 112 of the insert drape portion 102. For example, the insert drape portion may have tubing securement elements that function as a separation assistance member.

Figure 6:
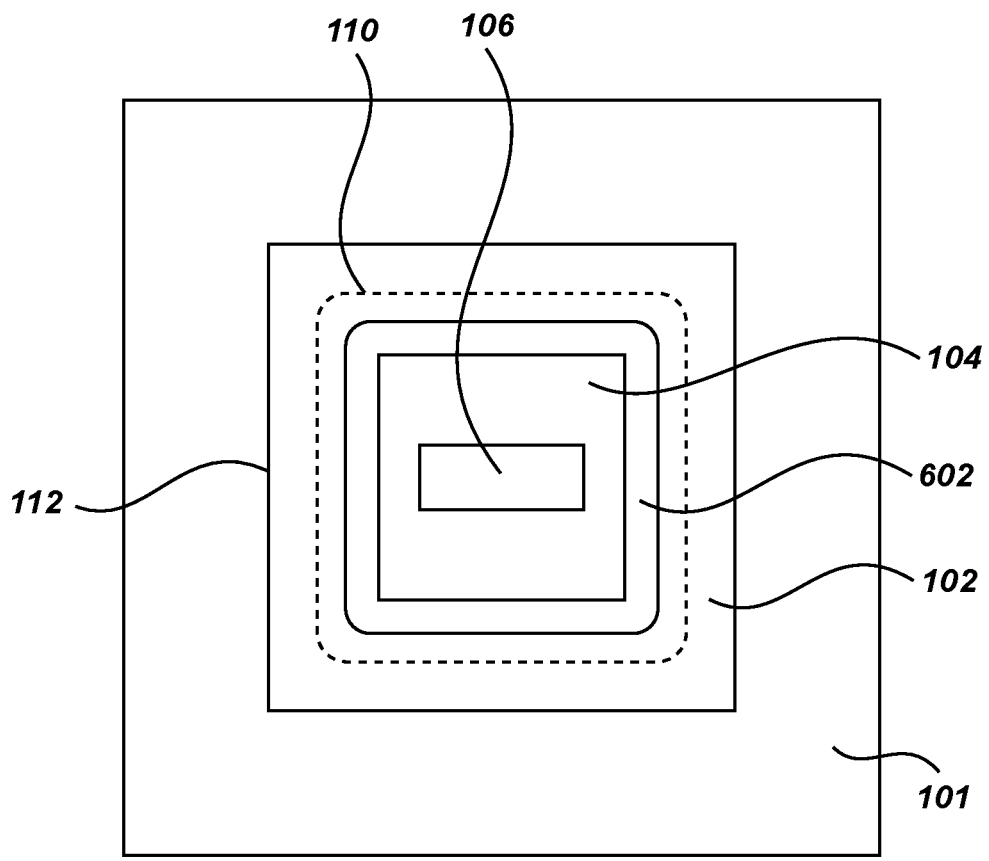
FIG. 6 is a plan view of the front side of a drape according to another embodiment.

In one embodiment, illustrated in FIG. 6, the insert drape portion 102 has a fluid retaining clement 602 which acts as a barrier or dam, preventing fluids from reaching or spreading from the insert drape portion to the base drape portion 101, which in this embodiment is biodegradable. The fluid retaining element 602 may be within the perimeter 110 of the void 104 of the base drape potions to prevent any fluid from contacting the base drape portion through the insert drape portion 102. The barrier may be absorbent material applied to one of the sides of the drape or incorporated therein. Alternatively, the barrier may be a thicker portion of the drape, or the barrier may be a fluid impervious material such as film.

Figure 7:
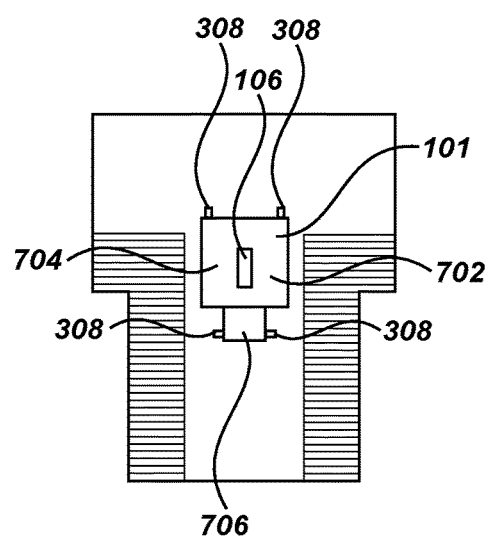
FIG. 7 is a plan view of the front side of a drape according to another embodiment in which the insert drape portion is a laparotomy drape portion.

Other exemplary embodiments of the drape system are shown in FIGS. 7-16. These embodiments are exemplary only and a person of ordinary skill in the art would readily recognize the application of the present invention to other procedures and drape configurations. FIG. 7 is a plan view of the front side of a drape according to an embodiment of the invention. In this embodiment, the base drape portion 101 has a T-shape and the insert drape portion is a laparotomy drape portion 702. The laparotomy drape portion 702 may include a first section 704, a second section 706 and tubing securement elements that may double as drape separation assistance members 308. The first section 704 of the laparotomy drape portion 702 includes a procedural site 106.

Figure 8:
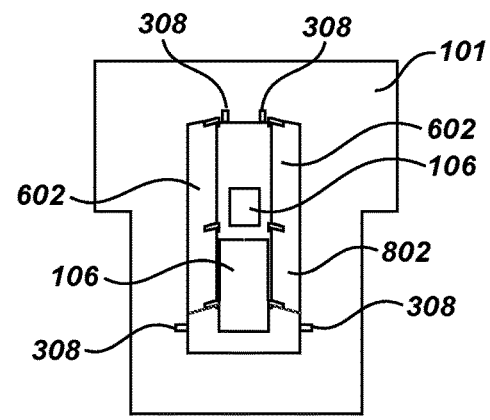
FIG. 8 is a plan view of the front side of a drape according to another embodiment in which the insert drape portion is a cardiovascular drape portion.

FIG. 8 is a plan view of the front side of a drape according to another embodiment. In this embodiment, the base drape portion 101 has a T-shape and the insert drape portion is a cardiovascular drape portion 802. The cardiovascular drape portion 802 may include fluid retaining elements 602, one or more procedural sites 106, and tubing securement elements that may double as drape separation assistance members 308.

Figure 9:
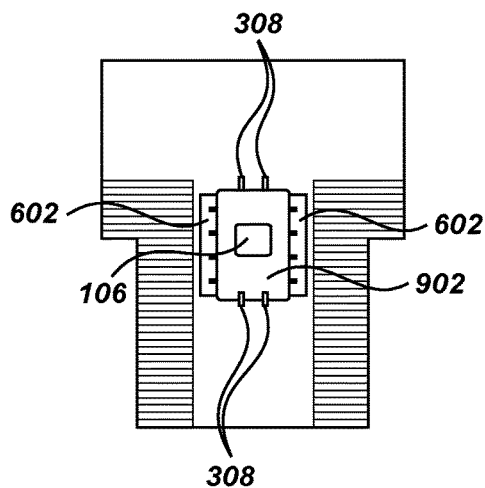
FIG. 9 is a plan view of the front side of a drape according to another embodiment in which the insert drape portion is a laparoscopic drape portion.

FIG. 9 is a plan view of the front side of a drape according to another embodiment. In this embodiment, the base drape portion 101 has a T-shape and the insert drape portion is a laparoscopic drape portion 902. The laparoscopic drape portion may include a procedural site 106, fluid retaining elements 602, and tubing securement elements that may double as drape separation assistance members 308.

Figure 10:
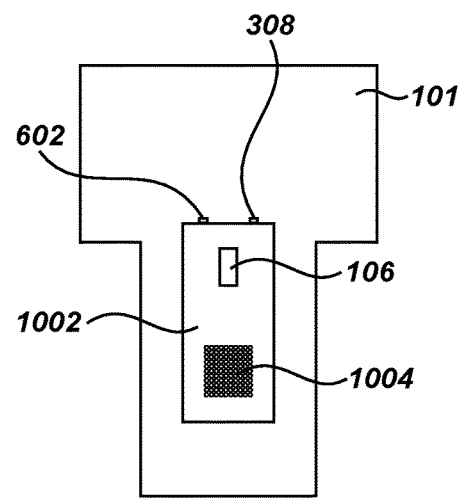
FIG. 10 is a plan view of the front side of a drape according to another embodiment in which the insert drape portion is a cystoscopy drape portion.

FIG. 10 is a plan view of the front side of a drape according to another embodiment. In this embodiment the base drape portion 101 has a T-shape and the insert drape portion is a cystoscopy drape portion 1002. The cystoscopy drape portion may include a procedural site 106, a non-slip instrument pad 1004, and tubing securement elements that may double as drape separation assistance members 308.

Figure 11:
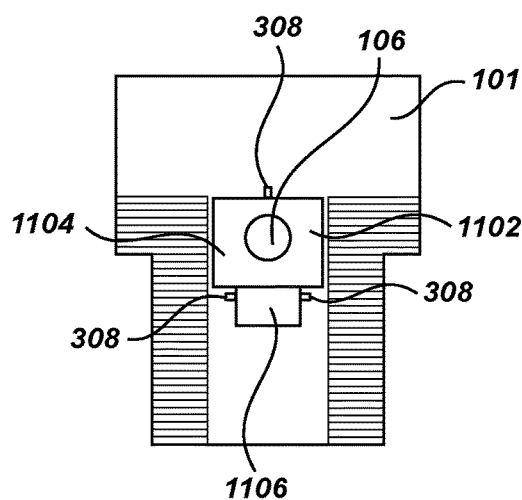
FIG. 11 is a plan view of the front side of a drape according to another embodiment in which the insert drape portion is a c-section drape portion.

FIG. 11 is a plan view of the front side of a drape according to another embodiment. In this embodiment the base drape portion 101 has a T-shape and the insert drape portion is a c-section drape portion 1102. The c-section drape portion 1102 may include a first section 1104 and a second section 1106 and tubing securement elements that may double as drape separation assistance members 308. The first section 1104 of the c-section drape portion 1102 includes a procedural site 106. The second section 1106 may comprise a pouch.

Figure 12:
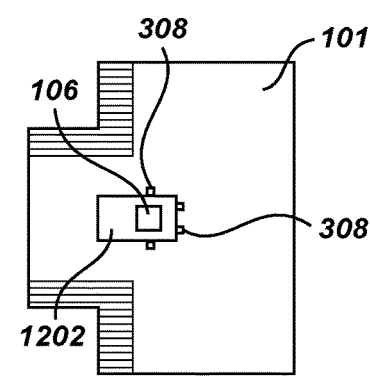
FIG. 12 is a plan view of the front side of a drape according to another embodiment in which the insert drape portion is a hand drape portion.

FIG. 12 is a plan view of the front side of a drape according to another embodiment. In this embodiment the base drape portion 101 has a T-shape and the insert drape portion is a hand drape portion 1202. The hand drape portion 1202 may include a procedural site 106 and tubing securement elements that may double as drape separation assistance members 308.

Figure 13:
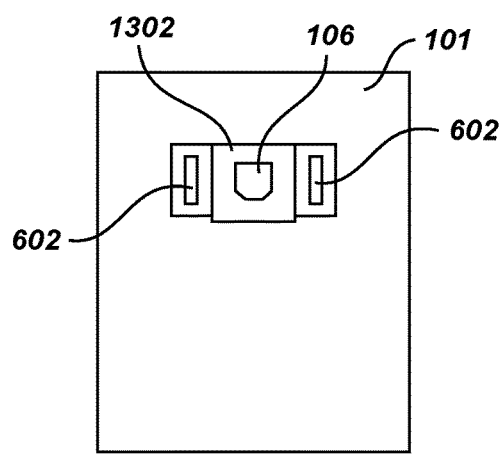
FIG. 13 is a plan view of the front side of a drape according to another embodiment in which the insert drape portion is an eye drape portion.

FIG. 13 is a plan view of the front side of a drape according to another embodiment. In this embodiment the base drape portion 101 is coupled to the insert drape portion, which is an eye drape portion 1302. The eye drape portion 1302 may include a procedural site 106 and fluid retaining elements 602, which may comprise fluid collection pouches.

Figure 14:
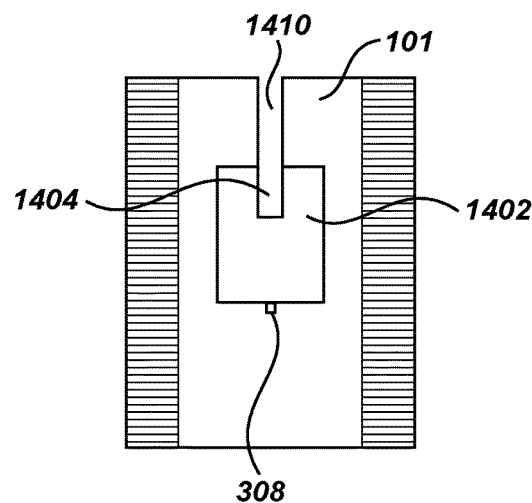
FIG. 14 is a plan view of the front side of a drape according to another embodiment in which the insert drape portion is a split drape portion.

FIG. 14 is a plan view of the front side of a drape according to another embodiment. In this embodiment the base drape portion 101 has a generally rectangular shape and includes a split 1410 extending from an edge. The base drape portion 101 is coupled to the insert drape portion, which is a split drape portion 1402. The insert split drape portion 1402 includes a split 1404 extending from an edge 112 that corresponds with the split 1410 extending from an edge of the base drape portion. The split drape portion 1402 may also include a tubing securement element that may double as a drape separation assistance member 308.

Figure 15:
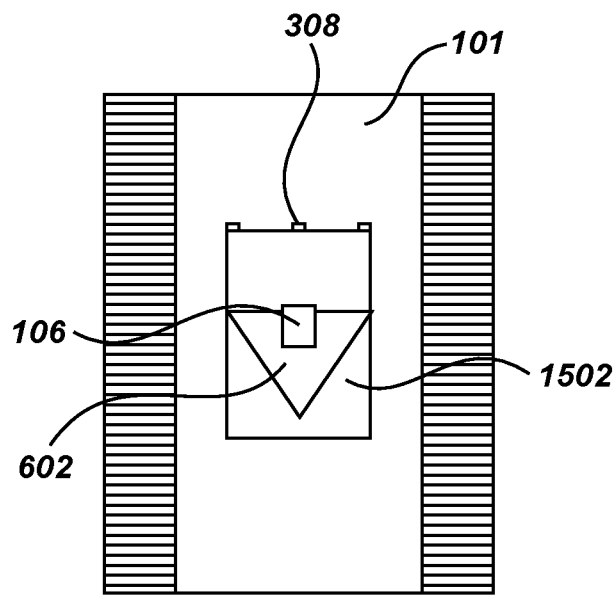
FIG. 15 is a plan view of the front side of a drape according to another embodiment in which the insert drape portion is an arthroscopy drape portion.

FIG. 15 is a plan view of the front side of a drape according to another embodiment. In this embodiment the base drape portion 101 has a square shape, and the insert drape portion is an arthroscopy drape portion 1502. The arthroscopy drape portion includes tubing securement elements that may double as drape separation assistance members 308. The arthroscopy drape portion 1502 may include a procedural site 106 and a fluid retaining element 602, which may comprise a fluid collection pouch.

Figure 16:
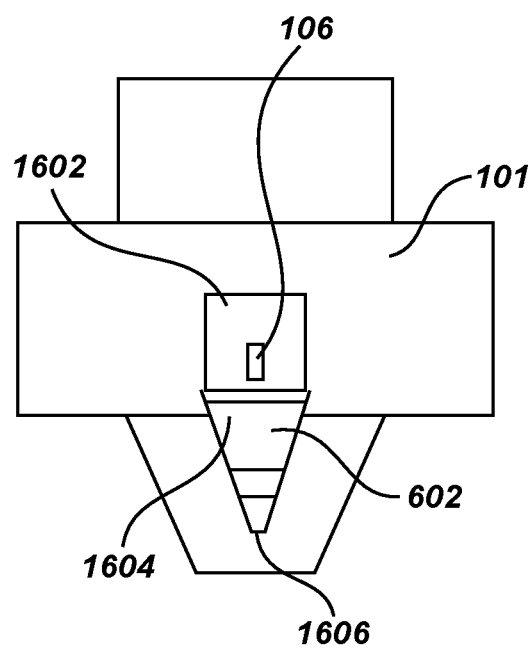
FIG. 16 is a plan view of the front side of a drape according to another embodiment in which the insert drape portion is a lithotomy drape portion.

FIG. 16 is a plan view of the front side of a drape according to another embodiment. In this embodiment the base drape portion 101 has a polygon shape and the insert drape portion is a lithotomy drape portion 1602. The lithotomy drape portion 1602 may include a procedural site 106 and a fluid retaining element 602, which may comprise a fluid fluid collection pouch 1604. The fluid fluid collection pouch 1604 may include a port 1606.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

What is claimed is:

1. A medical drape comprising:
a base drape portion having a front side, a back side, and a perimeter comprising a first side edge, a second side edge, a top edge, and a bottom edge, the first side edge and the second side edge being positioned opposite one another, the top edge and the bottom edge being positioned opposite one another, the base drape portion defining perforations such that the perforations separate the base drape portion into a first base drape portion and a second base drape portion, the second base drape portion surrounding the first base drape portion;
an insert drape portion removably attached to the base drape portion, the insert drape portion having a perimeter and a procedure access area disposed within the perimeter; and
a securement element selectively attaching the base drape portion to the insert drape portion,
wherein the perimeter of the base drape portion is larger than the perimeter of the insert drape portion.

2. The drape of claim 1 wherein the first base drape portion defines a void, the void having a perimeter comprising a first edge.

3. The drape of claim 2 wherein the insert drape portion covers the void of the first base drape portion.

4. The drape of claim 3 wherein the insert drape portion extends beyond the first edge of the void such that the insert drape portion overlaps the first base drape portion at least along the first edge of the void.

5. The drape of claim 4 wherein the perimeter of the insert drape portion extends beyond the perimeter of the first base drape portion void such that the insert drape portion overlaps the first base drape portion along substantially the entire perimeter of the void.

6. The drape of claim 1 wherein the base drape portion comprises a first material and the insert drape portion comprises a second material.

7. The drape of claim 6 wherein the insert drape portion comprises a bio-hazard containment portion.

8. The drape of claim 1 wherein the base drape portion comprises a biodegradable material.

9. The drape of claim 8 wherein the biodegradable material comprises a fluoro-chemical free material.

10. The drape of claim 1 wherein the securement element is an adhesive.

11. The drape of claim 1 wherein the securement element is a hook and loop fastener.

12. The drape of claim 1 wherein the securement element is a first securement element and further comprising a second securement element selectively attaching the base drape portion to the insert drape portion.

13. A protective drape comprising:
a first drape portion having a front side, a back side, and a perimeter,
the first drape portion including a first biodegradable material including cellulose,
the first drape portion defining perforations separating the first drape portion into an inner portion and an outer portion, the outer portion at least partially surrounding the inner portion;
a second drape portion; and
a securement element connecting the first drape portion to the second drape portion, the perforations surrounding the securement element.

14. The drape of claim 13 wherein the first biodegradable material comprises a biodegradable fluoro-chemical free drape material.

15. The drape of claim 13 wherein the first biodegradable material comprises unbleached cellulose.

16. The drape of claim 13 wherein the first biodegradable material comprises a wood pulp material.

17. The drape of claim 13 wherein the first biodegradable material comprises a biodegradable repellency resin.

18. The drape of the claim 13 wherein the first biodegradable material comprises a biodegradable wet-strength additive.

19. The drape of claim 13 wherein the first biodegradable material comprises a dye-free material.

20. The drape of claim 13 wherein the first biodegradable material has at least AMII standard level 3 characteristics.

21. A protective drape comprising:
a base drape portion comprising a first biodegradable material, the base drape portion defining perforations separating the base drape portion into a first base drape portion and a second base drape portion, the second base drape portion at least partially surrounding the first base drape portion;
an insert drape portion connected with the base drape portion; and
a securement element coupling the base drape portion to the insert drape portion.

22. The drape of claim 21 wherein the insert drape portion comprises a second material different than the first biodegradable material.

23. The drape of claim 22 wherein the second material comprises a non-biodegradable material.

24. A medical drape comprising:
a base drape portion having a front side, a back side, and a perimeter, the base drape portion defining perforations such that the perforations separate the base drape portion into a first base drape portion and a second base drape portion, the second base drape portion at least partially surrounding the first base drape portion;
a removable drape portion at least partially surrounded by the base drape portion and removable from the base drape portion, the removable drape portion having a perimeter and a procedure site disposed within the perimeter of the removable drape portion; and
a securement element coupling the base drape portion to the removable drape portion.

25. The drape of claim 24 wherein at least one of the base drape portion and the removable drape portion comprises a biodegradable material.

\* \* \* \* \*